United States Patent
O'Neill et al.

(10) Patent No.: US 11,839,730 B2
(45) Date of Patent: Dec. 12, 2023

(54) URETHRAL DELIVERY DEVICE

(71) Applicant: ASSURE MEDICAL LTD, Quin (IE)

(72) Inventors: Liam O'Neill, Midleton (IE); John O'Donoghue, Dungarvan (IE); Hugh Flood, Clonlara (IE); Gerard O'Keeffe, County Clare (IE)

(73) Assignee: ASSURE MEDICAL LTD. CO., Clare Quin (IE)

( * ) Notice: Subject to any disclaimer, the term of this patent is extended or adjusted under 35 U.S.C. 154(b) by 707 days.

(21) Appl. No.: 16/980,469

(22) PCT Filed: Mar. 15, 2019

(86) PCT No.: PCT/EP2019/055878
§ 371 (c)(1),
(2) Date: Sep. 14, 2020

(87) PCT Pub. No.: WO2019/175055
PCT Pub. Date: Sep. 19, 2019

(65) Prior Publication Data
US 2021/0015993 A1    Jan. 21, 2021

(30) Foreign Application Priority Data
Mar. 15, 2018   (GB) .................................... 1804165

(51) Int. Cl.
*A61M 31/00*   (2006.01)
*A61K 9/00*   (2006.01)
(Continued)

(52) U.S. Cl.
CPC ........... *A61M 31/00* (2013.01); *A61K 9/0034* (2013.01); *A61K 9/06* (2013.01); *A61K 31/155* (2013.01);
(Continued)

(58) Field of Classification Search
CPC .. A61M 31/00; A61M 3/0262; A61M 3/0279; A61M 3/0245; A61M 2205/0205;
(Continued)

(56) References Cited

U.S. PATENT DOCUMENTS 289,528 A * 12/1883 Goodner
2,895,280 A   12/1883 Goodner
(Continued)

FOREIGN PATENT DOCUMENTS

| CN | 2368536 Y | 3/2000 |
|---|---|---|
| DE | 2011119160 A1 | 5/2013 |
| FR | 423811 A | 4/1911 |

OTHER PUBLICATIONS

International Search Report dated Jun. 7, 2019 in corresponding International Patent App. No. PCT/EP2019/055878.

*Primary Examiner* — Dung T Ulsh
(74) *Attorney, Agent, or Firm* — MILES & STOCKBRIDGE P.C.; Ajay A. Jagtiani

(57) ABSTRACT

An urethral antimicrobial delivery device (1) comprising; a deformable reservoir (101) in fluid connection with an elongate member (102), the elongate member comprising a lumen, the elongate member having a proximal end and a distal end, the elongate member having a plurality of pores (103) defined therein, said pores being distributed along a length of said elongate member, the elongate member being dimensioned for insertion through an external urethral orifice of a female subject, whereby the elongate member is insertable into a distal urethral cavity for delivery of an antimicrobial in said distal urethral cavity, and wherein the device comprises a collar (105) to prevent said elongate member entering a proximal urethral cavity.

19 Claims, 4 Drawing Sheets

(51) Int. Cl.
*A61K 9/06* (2006.01)
*A61K 31/155* (2006.01)
*A61K 47/26* (2006.01)
*A61M 3/02* (2006.01)

(52) U.S. Cl.
CPC ........... *A61K 47/26* (2013.01); *A61M 3/0262* (2013.01); *A61M 3/0279* (2013.01); *A61M 3/0245* (2013.01); *A61M 2205/0205* (2013.01); *A61M 2205/075* (2013.01); *A61M 2210/1092* (2013.01)

(58) Field of Classification Search
CPC .... A61M 2205/075; A61M 2210/1092; A61K 9/0034; A61K 9/06; A61K 31/155; A61K 47/26
See application file for complete search history.

(56) References Cited

U.S. PATENT DOCUMENTS

| | | | |
|---|---|---|---|
| 9,629,953 B2 * | 4/2017 | Rucinski | A61M 3/0233 |
| 2006/0122563 A1 * | 6/2006 | Ziv | A61M 31/00 |
| | | | 604/187 |
| 2016/0058717 A1 * | 3/2016 | Page | A61K 9/0053 |
| | | | 514/632 |
| 2016/0199630 A1 * | 7/2016 | Cline | A61M 11/007 |
| | | | 604/125 |
| 2019/0046488 A1 * | 2/2019 | Rosenblatt | C08L 5/06 |

\* cited by examiner

URETHRAL DELIVERY DEVICE

CROSS-REFERENCE TO RELATED APPLICATIONS

This application is a National Stage of International Application No. PCT/EP2019/055878 filed on Mar. 15, 2019, which is hereby incorporated by reference in its entirety.

FIELD

The present invention relates to an antimicrobial delivery device, in particular, an urethral antimicrobial delivery device, designed for delivery of an antimicrobial in the lower urethra of a female subject.

BACKGROUND TO THE INVENTION

Conditions such as bladder pain syndrome, interstitial cystitis, urethritis, urethra pain syndrome are inflammatory conditions of the mucosal, submucosal and muscular layers of the bladder without the presence of detectable infectious pathogens. The cause of lower urinary tract inflammation is often, but not necessarily, triggered by an infection (bacterial cystitis). However, in a significant number of cases, the cause is unknown and diagnosis of the condition is regarded as a diagnosis of exclusion. Inflammation of the lower urinary tract is associated with urinary urgency, urinary frequency, waking at night to urinate (nocturia), and pain/discomfort during voiding (dysuria) and in the suprapubic area. Symptoms may overlap with other urinary bladder disorders (in both sexes) such as: urinary tract infection (UTI), overactive bladder and prostatitis.

The urinary tract is normally sterile. However, UTIs are one of the more common infections across all patient cohorts. Urinary tract infections (UTIs) are especially common in females, and cystitis (bladder infection) represents the majority of these infections. Related terms include pyelonephritis, which refers to upper urinary tract infection; bacteriuria, which describes bacteria in the urine (with or without symptoms); and candiduria, which describes yeast in the urine.

*Escherichia coli* causes the majority of uncomplicated cystitis cases. Among the pathogens responsible for the remainder are *Staphylococcus saprophyticus, Proteus mirabilis, Klebsiella pneumoniae,* or *Enterococcus faecalis.* Uropathogenic bacteria, derived from a subset of faecal flora, have traits that enable adherence, growth, and resistance of host defences. These traits facilitate colonization and infection of the urinary tract.

Adhesins are bacterial surface structures that enable attachment to host membranes. In *E. coli* infection, these include both pili (i.e. fimbriae) and outer-membrane proteins (e.g. Dr hemagglutinin). *P fimbriae*, which attach to globo-series-type glycolipids found in the colon and urinary epithelium, are associated with pyelonephritis and cystitis and are found in many *E. coli* strains that cause urosepsis.

Most complicated UTIs are nosocomial in origin. Increasingly, UTIs in patients in health care institutions and in those with frequent antibiotic exposure are caused by multidrug-resistant gram-negative pathogens, such as extended-spectrum beta-lactamase (ESBL) and carbapenemase producers. However, the prevalence of multidrug-resistant pathogens varies by locale. The most important risk factor for bacteriuria is the presence of a catheter. A large portion of nosocomial UTIs are related to urethral catheterization, while 5-10% are related to genitourinary manipulation. Catheters inoculate organisms into the bladder and promote colonization by providing a surface for bacterial adhesion and causing mucosal irritation. UTIs are the most common type of bacterial infection and occur in approximately 50-60% of women over their lifetime. These infections are normally treated with systemic antibiotics and recovery is usually complete. However, there is a group of patients who suffer from recurrent UTIs. A recurrent urinary tract infection (RUTI) defined as 2 culture-proven UTIs in 6 months or 3 in 12 months. These patients can find their lives to be significantly disrupted and the only effective treatments for RUTIs at this point are PRN (short term courses of antibiotics as needed) or long-term prophylactic antibiotics (subject to sensitivity).

Most recurrences occur within the first 3 months after treatment and about 90% of the time are re-infections, i.e. infection with a different organism at any time or the same organism more than 2 weeks after clearance of infection from the urine after treatment. Where infection with the same organism occurs within 2 weeks of treatment, persistence or relapse of infection is said to occur. Risk factors include sexual activity, use of spermicides, non-secretor status (associated with facilitated bacterial cell surface binding) and prior antibiotic exposure.

*E. Coli* is the causative organism in 80-90% of community-acquired cases. Uropathogenic *E. Coli* (UPEC) are such most likely by virtue of the presence of flagellae, surface antigens expressed on fimbriae or the cell wall or just by virtue of being the most prevalent faecal clones.

The currently accepted mechanism for infection and re-infection is transfer of UPEC from the rectum to the anus-→perineum→introitus→vagina→urethral meatus and distal urethra. The epithelial lining of the latter is identical to and continuous with the non-keratinising, stratified, squamous epithelium of the vagina. The transitional cell layer lines the upper third or so of the urethra and is continuous with the transitional cell layer of the bladder.

Normally, resident *E. Coli* and other microbes are non-pathogenic, do not transgress beyond the distal urethra and function as true commensals. However, when UPEC replace commensals and their entry is facilitated to the bladder via the urethra during sexual activity (75% instances), UTI results. Symptomatic UTI (burning pain, frequency, urgency) requires attachment of the bacteria to specific polysaccharide receptors on the umbrella cell surface layer of the transitional epithelium followed by penetration of the cell membrane to set up an inflammatory reaction. Symptoms and signs of UTI in the adult are as follows:

Dysuria
Urinary urgency and frequency
A sensation of bladder fullness or lower abdominal discomfort
Suprapubic tenderness
Flank pain and costovertebral angle tenderness (may be present in cystitis but suggest upper UTI)
Bloody urine
Fevers, chills, and malaise (may be noted in patients with cystitis, but more frequently associated with upper UTI)

Oral therapy with an empirically chosen antibiotic that is effective against gram-negative aerobic coliform bacteria (e.g. *E. coli*) is the principal treatment intervention in patients with cystitis. The first-choice agents for treatment of uncomplicated acute cystitis in women include the following:

Nitrofurantoin monohydrate/macrocrystals
Trimethoprim-sulfamethoxazole (TMP-SMX)
Co-amoxyclav
Cephalexin
Fosfomycin However, systemic dosing with antibiotics does cause concerns, especially around the issue of antibiotic resistance. Bladder instillation of pharmaceutical agents is one of the main forms of treatment of lower urinary tract inflammation. Advantages of this treatment approach include direct contact of the medication with the bladder wall and decreased risk of systemic side effects. Bladder instillations use a transurethral approach where a drug is instilled directly into the bladder using a catheter tube on several occasions and localised delivery of therapeutics can eradicate the infection in some patients.

Although uncomplicated lower UTI (cystitis) may resolve spontaneously, effective treatment lessens the duration of symptoms and reduces the incidence of progression to upper UTI. Even with effective antibiotic treatment, however, at least 25% of women with cystitis will experience a recurrence.

Many patients with cystitis suffer from repeated flare ups. It is estimated that approximately 60% of women will acquire a bladder infection at some time during their life, with as many as 15-20% of women will have problems with recurrent infections. As outlined above, cystitis is said to be recurrent when a woman has had two proven infections within six months, or three infections in a year.

For women who develop recurrent infections, the usual cause is repeated new episodes of bacterial infection of the bladder. There is a common misconception that recurrent bladder infection is due to an inadequately treated infection. However, repeat infection is usually due to a new episode of infection which occurs once the previous one has been treated. Several recognized initiating events can trigger infection. The most common is sexual intercourse. It appears that the pressure in the vaginal area which occurs at intercourse may facilitate ascent of bacteria up the urethra into the bladder. Some women report that they develop bladder infection almost every time that they have intercourse and this can have devastating effects upon relationships.

Prophylactic antibiotic use can help reduce the problem but it is not ideal as there is a concern that frequent exposure to antibiotics can promote the evolution of antibiotic resistant bacteria. In addition, the therapeutic drugs may in and of themselves give rise to sensitisation of the mucosal tissue surrounding the urethra or produce antibiotic allergy with long term use. Together, antibiotic resistance and allergy may render treatment ineffective or impossible in up to 34% of cases.

Accordingly, there is a pressing need to provide improved treatments including prophylactics to reduce the likelihood of urinary tract infection in women. The present invention provides a device and methods to address this need.

SUMMARY OF THE INVENTION

In one aspect, the present invention provides an urethral antimicrobial delivery device comprising: a deformable reservoir in fluid connection with an elongate member, the elongate member comprising a lumen, the elongate member having a proximal end and a distal end, the elongate member having a plurality of pores defined therein, said pores being distributed along a length of said elongate member, the elongate member being dimensioned for insertion through an external urethral orifice of a female subject, whereby the elongate member is insertable into a distal urethral cavity for delivery of an antimicrobial in said distal urethral cavity.

Suitably, the device comprises a collar to prevent said elongate member entering the proximal urethral cavity.

For example, the present invention provides an urethral antimicrobial delivery device comprising: a deformable reservoir in fluid connection with an elongate member, the elongate member comprising a single lumen, wherein the elongate member is of from 15 mm to 40 mm in length, the elongate member having a proximal end and a distal end, the elongate member having a plurality of pores defined therein, said pores being distributed along a length of said elongate member, the elongate member being dimensioned for insertion through an external urethral orifice of a female subject, whereby the elongate member is insertable into a distal urethral cavity for delivery of an antimicrobial in said distal urethral cavity; and wherein the device comprises a collar to prevent said elongate member entering the proximal urethral cavity.

The device may be employed to deliver a composition to the distal urethral cavity of a female subject. Advantageously, the above device may be employed for topical delivery of an antimicrobial in the distal urethral cavity of a female subject, prior to engaging in sexual activity, such as intercourse, thereby reducing the likelihood of the subject developing a urinary tract infection. The antimicrobial may be an antimicrobial composition comprising an antimicrobial agent. An antimicrobial, such as an antimicrobial gel, may be stored in the device, and the device may be employed to topically apply said antimicrobial in the distal urethral cavity of a female subject. The device is configured to enable the subject to self-administer a single topical application of an antimicrobial in their distal urethral cavity. The device is a disposable device, designed for a single use. Suitably, the device is sterilised. Accordingly, the device is sterile, prior to use, and therefore will not itself be a potential source of infection.

The elongate member may be tapered such that the diameter of the distal end of the elongate member is of smaller diameter than the diameter of the proximal end of said elongate member. Advantageously, the tapered elongate member facilitates easy insertion into the urethral cavity, through the urethral orifice.

The pores are distributed along the length of the elongate member, and advantageously, the pores may be offset with respect to each other. This ensures optimal delivery of an antimicrobial agent from the device. The pores are configured to ensure circumferential delivery of an antimicrobial device from the elongate member.

In one embodiment, the elongate member may be capped at the terminus of the distal end, for example by a plate member. This configuration provides an elongate member having a closed terminus (i.e. there are no pores (or orifices) in the plate member which caps the terminus of the distal end) and ensures that the antimicrobial may be delivered exclusively through the pores defined in the elongate member.

Alternatively, in a preferred embodiment, the elongate member may comprise a terminal orifice defined therein at the distal end of the elongate member. This ensures delivery of an antimicrobial from the terminus of the device into the urethral cavity in addition to circumferential delivery of the antimicrobial from the elongate member, thereby ensuring the antimicrobial is effectively and efficiently delivered within the entire distal urethral cavity including the urethral mucosal infoldings. The diameter of the terminal orifice may be similar in size to the diameter of the pores, or indeed the diameter of the terminal orifice may be shorter in length than the diameter of the pores defined in said elongate member, this arrangement is advantageous as it encourages an antimicrobial agent to flow from pores along the length of the elongate member. The elongate member may comprise a plurality of terminal orifices defined therein at the distal end of the elongate member, for example, the elongate member may comprise two or three or more orifices defined therein. Suitably, the terminus of the elongate member may be capped with a plate comprising a plurality of terminal orifices defined within the plate.

The pores may have a diameter in the range of from 0.1 mm to 2.0 mm, such as from 0.5 mm to 1.8 mm, or from 0.5 mm to 1.5 mm. When the diameter is lower than 0.1 mm, delivery of the antimicrobial is too slow, and when the diameter is greater than 2.0 mm, delivery of the antimicrobial occurs too rapidly.

The collar of the device prevents the elongate member entering the proximal urethral cavity. The collar may be disposed in the range of from 15 mm to 40 mm from the terminus of the distal end of the elongate member. When the elongate member of the device is fully inserted into a urethral cavity of a female subject, the collar of the device abuts the urinary meatus. This abutment against the exterior of the urethral orifice ensures that the elongate member cannot be inserted too far into the urethral tract, beyond the mid-urethral sphincter and into the proximal urethral cavity. Suitably, the elongate member is dimensioned such that it may extend a distance of from 10 mm to 40 mm into the urethral cavity, such as from 15 mm to 20 mm into the urethral cavity. If the elongate member was longer in length than 40 mm, this could lead to insertion of the elongate member into the proximal urethral cavity which is not desirable. If the elongate member is less than 15 mm in length, the ease of insertion into the female urethral cavity decreases, and the delivery of an antimicrobial from the device is less effective.

The deformable reservoir is suitable for storing an antimicrobial, such as an antimicrobial gel. Suitably, the deformable reservoir comprises an internal volume in the range of from 0.5 mL to 5 mL, preferably 1.8 mL to 3.2 mL, such as from 2 mL to 3 mL. The antimicrobial may be delivered from the device for example, by squeezing the deformable reservoir. The reservoir is arranged such that a female subject may self-administer a single topical application of an antimicrobial in their distal urethral cavity. Once the elongate member has been inserted into the distal urethral cavity, the user/operator may topically apply the antimicrobial in their distal urethral cavity by squeezing the deformable reservoir.

Suitably, the collar and the deformable reservoir are integrally formed.

The elongate member may have an external diameter in the range of from 3.0 mm to 5.0 mm, preferably from 4.0 mm to 4.7 mm. For embodiments where the elongate member is tapered, the person skilled in the art will appreciate the external diameter will vary, however, suitably the external diameter of any point along the elongate member will be in the range of from 3.0 mm to 5.0 mm, preferably from 4.0 mm to 4.7 mm.

As outlined above, the antimicrobial delivery device may comprise an antimicrobial. The antimicrobial may be an antimicrobial agent, or for example a composition comprising an antimicrobial agent, such as an antimicrobial gel. The antimicrobial comprises an antimicrobial agent. The antimicrobial may comprise at least one antimicrobial agent selected from the group consisting of antiseptics such as chlorhexidine, povidone-iodine, glutaraldehyde, chloroxylenol, silver ions, benzalkonium chloride, cetylpyridinium chloride cetalkonium chloride, triclosan, lauric acid, benzethonium chloride, sodium hypochlorite and antibiotics such as neomycin, bacitracin, polymyxin, penicillin, mupirocin, fusidic acid and combinations thereof.

For example, the antimicrobial may comprise an antimicrobial gel comprising at least one antimicrobial agent selected from the group consisting of antiseptics such as chlorhexidine, povidone-iodine, glutaraldehyde, chloroxylenol, silver ions benzalkonium chloride, cetylpyridinium chloride cetalkonium chloride, triclosan, lauric acid, benzethonium chloride, sodium hypochlorite and antibiotics such as neomycin, bacitracin, polymyxin, penicillin, mupirocin, fusidic acid and combinations thereof.

The antimicrobial may comprise an antimicrobial composition. The antimicrobial composition may comprise a sugar such as mannose. This sugar may be added in concentrations of 0.01 wt % or more to 50 wt % or less, for example the sugar may be added in a concentration of from 0.1 wt % or more, such as 0.5 wt % or more, or 1 wt % or more, for example 5 wt % or more based on the total weight of the antimicrobial composition. The sugar may be added in a concentration of 50 wt % or less such as 30 wt % or less, suitably 15 wt % or less, for example 10 wt % or less, or 8 wt % or less based on the total weight of the antimicrobial composition. For example, the sugar may be present in a concentration of from 0.01 to 8 wt % based on the total weight of the antimicrobial composition.

Suitably, the antimicrobial composition is an antimicrobial gel comprising a sugar such as mannose. This sugar may be added in concentrations of 0.01 wt % or more to 50 wt % or less, for example the sugar may be added in a concentration of from 0.1 wt % or more, such as 0.5 wt % or more, or 1 wt % or more, for example 5 wt % or more based on the total weight of the antimicrobial gel. The sugar may be added in a concentration of 50 wt % or less such as 30 wt % or less, suitably 15 wt % or less, for example 10 wt % or less, or 8 wt % or less based on the total weight of the antimicrobial gel. For example, the sugar may be present in a concentration of from 0.01 to 8 wt % based on the total weight of the antimicrobial gel. Without being bound by theory, it is thought that sugars, such as mannose may preferentially bind to virulent *E. coli* bacteria and thereby prevent them from migrating to the proximal urethra and into the bladder. The bacteria may then be eliminated by an antimicrobial agent in the gel.

Suitably, the antimicrobial agent is present in the antimicrobial composition at a concentration in the range of from 0.01 wt % to 1.0 wt % based on the total weight of the antimicrobial composition. Preferably, the antimicrobial agent is present in the antimicrobial composition at a concentration in the range of from 0.01 wt % to 0.5 wt %, such as from 0.1 wt % to 0.3 wt % based on the total weight of the antimicrobial composition. The antimicrobial agent may be present in an amount of from 0.05 wt % to 0.25 wt % based on the total weight of the antimicrobial composition.

For example, the antimicrobial agent may be present in an antimicrobial gel at a concentration in the range of from 0.01 wt % to 1.0 wt % based on the total weight of the antimicrobial gel. Preferably, the antimicrobial agent is present in the antimicrobial gel at a concentration in the range of from 0.01 wt % to 0.5 wt %, such as from 0.1 wt % to 0.3 wt % based on the total weight of the antimicrobial gel. The antimicrobial agent may be present in an amount of from 0.05 wt % to 0.25 wt % based on the total weight of the antimicrobial gel.

The antimicrobial gel may have a viscosity in the range of from about 35 cP to about 3500 cP when measured at 25° C., such as from about 100 cP to about 1000 cP when measured at 25° C. Suitably, the antimicrobial gel has a viscosity in the range of from about 400 cP to 800 cP when measured at 25° C.

In a preferred embodiment, the antimicrobial agent comprises chlorhexidine.

The antimicrobial composition may comprise: an antimicrobial agent in an amount of from 0.01 wt % to 1.0 wt % based on the total weight of the composition, a gelling agent in an amount of from 0.5 wt % to 30 wt % based on the total weight of the composition, and a pharmaceutically acceptable carrier.

The antimicrobial composition may comprise an antimicrobial agent comprising chlorhexidine, suitably the chlorhexidine is present in an amount of from 0.1 wt % to 0.3 wt % based on the total weight of the composition, a gelling agent comprising hydroxyethylcellulose which is present in an amount of from about 1 wt % to about 2.5 wt %, and a pharmaceutically acceptable carrier comprising water.

Suitably, the antimicrobial composition comprises one or more preservatives.

In preferred embodiments, the antimicrobial composition is water soluble, for example the antimicrobial gel is water soluble. Accordingly, when a subject urinates the barrier formed by the antimicrobial composition in the urethral cavity of the subject will be completely flushed from said cavity.

The urethral antimicrobial delivery device may comprise an antimicrobial gel, comprising chlorhexidine in a concentration of from 0.01 wt % to 1.0 wt % based on the total weight of the antimicrobial gel, said antimicrobial gel having a viscosity in the range of from 400 cP to 800 cP when measured at 25° C.

The deformable reservoir may comprise a seal, to retain antimicrobial within the reservoir. The seal may be broken once pressure is exerted on said reservoir, for example, when the user squeezes the reservoir, to thereby enable an antimicrobial stored within the reservoir to flow from the reservoir into the elongate member. Advantageously, the presence of the seal increases the shelf-life of an antimicrobial stored within the deformable reservoir of the delivery device.

In another aspect, the present invention provides a kit comprising the urethral antimicrobial delivery device described herein, said urethral delivery device comprising an antimicrobial gel, wherein said device is sterile and packaged in a sealed sterile packaging. Optionally, the kit may additionally comprise one or more condoms and/or lubricant.

In a further aspect, the present invention provides the urethral antimicrobial delivery device as described herein for use in treating, preventing or reducing the likelihood of urinary tract infection. The urethral antimicrobial delivery device for use in treating, preventing or reducing the likelihood of urinary tract infection may comprise an antimicrobial composition. The antimicrobial composition may comprise an antimicrobial gel. The antimicrobial agent in the antimicrobial composition may comprise chlorhexidine. The antimicrobial gel may comprise mannose.

Use of an urethral antimicrobial delivery device as described herein for treating, preventing or reducing the likelihood of urinary tract infection is also provided.

A method for treating, preventing or reducing the likelihood of urinary tract infection comprising employing an urethral antimicrobial delivery device as described herein, to topically apply an antimicrobial in a distal urethral cavity of a female subject is also provided.

Also provided herein is a method for treating, preventing or reducing the likelihood of urinary tract infection comprising employing an urethral antimicrobial delivery device as described herein, to topically apply an antimicrobial in a distal urethral cavity of a female subject, in combination with oral administration to said subject of mannose. For example, the subject may be treated with alpha D-mannose. Advantageously, the mannose binds bacteria such as uropathogenic E. coli which are subsequently excreted during urination.

In another aspect, the present invention provides a method for treating, preventing or reducing the likelihood of urinary tract infection comprising: intravesical administration of an antibiotic to a female subject in need thereof, said antibiotic being administered following engagement by said female subject in sexual activity, said antibiotic being administered optionally within 8 hours of engaging in said sexual activity, suitably within 3 hours, preferably within 1 hour of engaging in said sexual activity, and said antibiotic being administered following urination by said subject; whereby said antibiotic is administered using an intravesical delivery device comprising: a deformable reservoir in fluid connection with an elongate member, the elongate member comprising a lumen, the elongate member having a proximal end and a distal end, the elongate member having a plurality of pores defined therein, said pores being distributed along a length of said elongate member, the elongate member being dimensioned for insertion through an external urethral orifice of a female subject, said elongate member having a length of from 50 mm to 70 mm.

Suitably, the plurality of pores of the intravesical delivery device, are defined in the distal end of the elongate member. Advantageously, when the plurality of pores are defined in the distal end of the elongate member of the intravesical delivery device, a therapeutic may be exclusively delivered to the bladder.

The elongate member of the intravesical delivery device is dimensioned to facilitate entry of the distal end of the elongate member into the bladder. The plurality of pores in the elongate member, particularly those in the distal end of said elongate member facilitate uniform delivery of a therapeutic such as an antibiotic to the bladder.

Suitably, the antibiotic is selected from tobramycin, vancomycin, gentamicin, ampicillin, amoxicillin, Bactrim, carbapenems, chloramphenicol, cephalosporin C, cephalexin, cefaclor, cefamandole and ciprofloxacin, dactinomycin, actinomycin D, daunorubicin, doxorubicin, idarubicin, penicillins, piperacillin, streptomycin, cephalosporins, quinolones, anthracyclines, mitoxantrone, tetracyclines, ticarcillin, bleomycins, plicamycin (mithramycin), mitomycin, polymyxin, ciprofloxacin, or one or more antibiotics chosen from the family of penicillins, macrolides, tetracyclines, cephalosporins, fluoroquinolones, glycopeptides or aminoglycan antibiotics and mixtures thereof.

The intravesical antibiotic administration may be carried out within approximately 8 hours of engaging in sexual activity. Suitably, the method involves intravesical antibiotic administration to the female subject shortly after said subject has engaged in sexual activity, such as sexual intercourse. For example, 2 hours or less after engaging in sexual activity, preferably the antibiotic is administered less than 1.5 hours, for example, less than 1 hour, suitably less than 30 minutes after engaging in sexual activity. Suitably, the antibiotic is administered less than 1 hour following urination by the subject, preferably less than 30 minutes following urination by the subject, such as within 15 minutes following urination. Most preferably, the antibiotic is administered within 5 minutes following urination by the subject.

Also provided herein is a method for treating, preventing or reducing the likelihood of urinary tract infection in a female subject comprising the following steps:
(i) employing an urethral antimicrobial delivery device as described herein, to deliver an antimicrobial in a distal urethral cavity of a female subject prior to engaging in sexual activity;
(ii) flushing the antimicrobial from the distal urethral cavity by urination following said sexual activity; and
(iii) following urination, intravesical administration of an antibiotic to said subject optionally within 8 hours of engaging in said sexual activity, suitably within 3 hours, preferably within 1 hour of engaging in sexual activity, wherein said antibiotic is administered using an intravesical delivery device, comprising: a deformable reservoir in fluid connection with an elongate member, the elongate member comprising a lumen, the elongate member having a proximal end and a distal end, the elongate member having a plurality of pores defined therein, said pores being distributed along a length of said elongate member, suitably said plurality of pores being defined in the distal end of the elongate member, the elongate member being dimensioned for insertion through an external urethral orifice of a female subject, said elongate member having a length of from 50 mm to 70 mm.

Yet a further aspect of the present invention is a an intravesical delivery device, comprising: a deformable reservoir in fluid connection with an elongate member, the elongate member comprising a lumen, the elongate member having a proximal end and a distal end, the elongate member having a plurality of pores defined therein, said pores being distributed along a length of said elongate member, the elongate member being dimensioned for insertion through an external urethral orifice of a female subject, said elongate member having a length of from 50 mm to 70 mm.

Suitably said plurality of pores being defined in the distal end of the elongate member.

As outlined above, the intravesical delivery device may be used to treat, prevent or reduce the likelihood of urinary tract infection in a female subject.

The intravesical delivery device may also be used to treat recurrent bladder cancer or interstitial cystitis, whereby the device may be used to deliver therapeutics to the bladder. Advantageously, the device may be used to self-administer therapeutics, thereby significantly reducing the cost associated with such treatments. For example, the intravesical delivery device may be used to administer agents such as *Bacillus* Calmette-Guerin (BCG) for treating bladder cancer.

In preferred embodiments, the intravesical delivery device comprises a pharmaceutically composition comprising a therapeutic, such as an antibiotic and a pharmaceutically acceptable carrier. For example the pharmaceutical composition may comprise an antibiotic and a pharmaceutically acceptable carrier. The pharmaceutical composition may for example be in liquid or gel form. Suitably, the intravesical delivery device comprises a pharmaceutical composition formulated in as a liquid, and the device further comprises a gel plug which acts as a barrier to prevent premature emptying of the pharmaceutical composition. Following insertion of the distal end of the elongate member of the intravesical delivery device into the bladder, the user may deform the deformable reservoir wherein the pharmaceutical composition is stored, leading to expulsion of said composition from the device via the pores and orifices in said elongate member into the bladder. In some embodiments, the elongate member of the intravesical delivery device comprises a gel plug which prevents premature expulsion/delivery of the pharmaceutical composition which is stored in the deformable reservoir from the intravesical delivery device, prior to insertion of the proximal end of the elongate member into the bladder. In such an embodiment, when the elongate member is suitably positioned, with the distal end thereof in the bladder of the subject, the deformable reservoir may be deformed leading initially to flushing of the gel plug from the elongate member followed by expulsion/delivery of the pharmaceutical composition from the intravesical delivery device into the bladder.

Suitably, the intravesical delivery device has a hemispherical terminus at the distal end of the elongate member, said hemispherical terminus comprising two or more orifices defined therein. This configuration advantageously ensures the terminus of the distal end of the elongate member acts as a spray head, which ensures optimal delivery in three-dimensional space.

BCG treatment involves intravesical delivery of BCG to a patient. In order to get optimal effectiveness BCG should be administered in an empty bladder. The hemispherical terminus comprising two or more orifices defined therein advantageously ensures a three-dimensional spray of the BCG treatment will be delivered into the bladder and thereby coat the internal walls of the bladder.

Other treatments such as DMSO (dimethylsulfoxide), chondroitin sulphate or hyaluronic acid could also be administered using the intravesical delivery device of the present invention.

The elongate member of the intravesical delivery device may be tapered such that the diameter of the distal end of the elongate member is of smaller diameter than the diameter of the proximal end of said elongate member.

The pores distributed along the length of said elongate member may be offset.

The diameter of the orifices defined in the hemispherical terminus may be shorter in length than the diameter of the pores defined in said elongate member. Suitably, the hemispherical terminus comprises from 3 to 12 orifices defined therein.

Suitably, pores are distributed along the distal end of the elongate member of the intravesical delivery device. For example, in an intravesical device according to the present invention where the elongate member is from 50 mm to 70 mm in length, the pores may be distributed within 10 mm to 20 mm from the terminus of the distal end. This ensures optimal delivery of a therapeutic/payload to the bladder.

In yet a further aspect the present invention provides, a kit comprising the urethral antimicrobial delivery device described herein, and an intravesical delivery device, comprising: a deformable reservoir in fluid connection with an elongate member, the elongate member comprising a lumen, the elongate member having a proximal end and a distal end, the elongate member having a plurality of pores defined therein, said pores being distributed along a length of said elongate member, the elongate member being dimensioned for insertion through an external urethral orifice of a female subject, said elongate member having a length of from 50 mm to 70 mm.

Suitably, said kit further comprises an antimicrobial, such as an antimicrobial composition as described herein. Suitably, the kit further comprises an antibiotic. In preferred embodiments, the kit comprises an urethral antimicrobial delivery device comprising an antimicrobial composition, and an intravesical delivery device comprising an antibiotic.

BRIEF DESCRIPTION OF THE DRAWINGS

Embodiments of the invention will be described, by way of example only, with reference to the accompanying drawings in which.

DESCRIPTION

Figure 1:
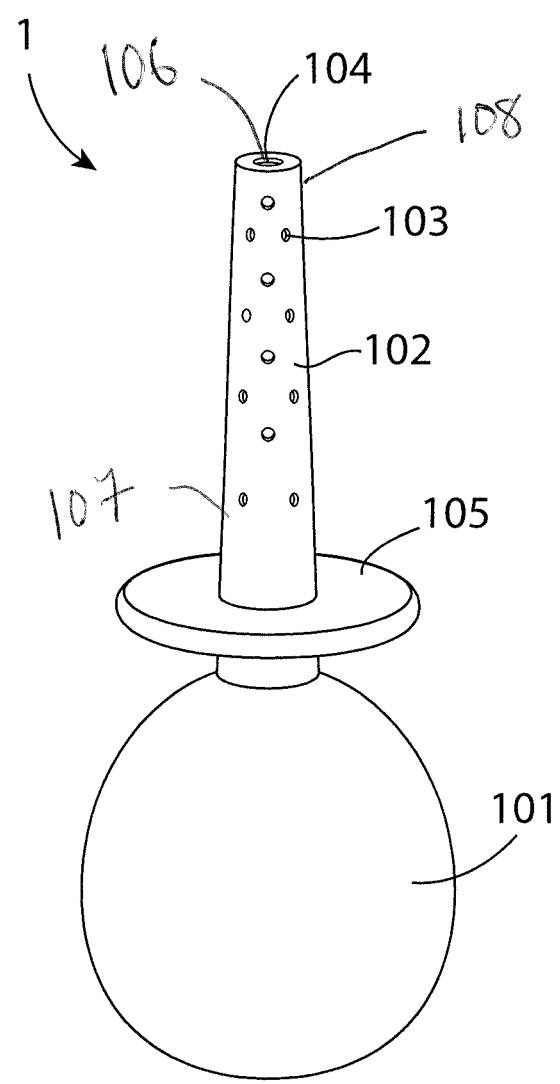
FIG. 1 is a perspective view of the antimicrobial delivery device.

As outlined above, there remains a desire for reducing recurrent UTIs in women. Prophylactic antibiotic use can help reduce the problem but this approach is not preferred, as sensitization to antibiotics can occur. Administering some classes of antibiotics to pregnant women is not advisable, as some antibiotics may be teratogenic. Furthermore, the prevalence of UTIs in pregnant women is higher than in non-pregnant women. Thus preventing the need for using antibiotics would be desirable, in particular, by preventing an infection from occurring in patients in the first instance.

Since the bladder is normally sterile, it is only when bacteria physically ascend from the urethra into the bladder that an infection typically occurs. Outside of nosocomial and catheter related infections, research has shown that one of the main factors giving rise to infections is sexual intercourse. During sex, the physical contact between participants and fluid flow can physically transfer bacteria from the anus, the vaginal introitus and other skin areas into the urethra and into the bladder, thereby initiating a urinary tract infection. This is often referred to as "honeymoon cystitis".

One potential method to prevent the ascension of the bacteria into the upper urethra and bladder is to physically impede their access. A physical blockage of the lower urethra would prevent the bacteria gaining access to the internal portion of the urethra and bladder. Given the micron size nature of the invading bacteria, complete blockage of the urethra would require a sub-micron alignment of the barrier with the internal wall. This would be difficult to achieve with a physical plug, as the plug has to be small enough to fit comfortably into the urethra and may itself act as a surface along which bacteria may migrate. However, a device that blocks the bulk of the urethral opening and lower urethra and is removed shortly after intercourse could significantly reduce bacterial ascension into the upper urethra and bladder.

A further option is to incorporate a temporary barrier into the distal portion of the urethra, which reduces the likelihood of UTI, by discouraging bacterial migration into the proximal urethral cavity and on to the bladder. The present invention provides such a means for introducing such a barrier.

References herein to an antimicrobial should be construed as referring to an antimicrobial agent or a composition comprising an antimicrobial agent i.e. the antimicrobial may be an antimicrobial agent or a composition comprising an antimicrobial agent.

As outlined above, the present invention provides an urethral antimicrobial delivery device comprising a deformable reservoir in fluid connection with an elongate member, the elongate member comprising a lumen, the elongate member having a proximal end and a distal end, the elongate member having a plurality of pores defined therein, said pores being distributed along a length of said elongate member, the elongate member being dimensioned for insertion through an external urethral orifice, whereby the elongate member is insertable into a distal urethral cavity for topical delivery of an antimicrobial in said distal urethral cavity; and wherein the device comprises a collar to prevent said elongate member entering a proximal urethral cavity.

The device facilitates delivery of a temporary barrier into the distal portion of the urethra, which reduces the likelihood of UTI, by discouraging bacterial migration into the proximal urethral cavity and on to the bladder. The barrier is a water soluble gel, and said gel can be inserted into the distal urethra prior to intercourse where it forms a physical barrier that prevents migration of bacteria into the distal urethra. The barrier can be readily removed subsequent to sexual activity by urinating. In preferred embodiments the water soluble gel comprises an antimicrobial—i.e. the barrier comprises a water soluble antimicrobial gel.

The device facilitates topical administration of an antimicrobial in the distal urethral cavity. The antimicrobial is preferably a gel. Prior to engaging in intercourse, a female subject may employ the antimicrobial delivery device to administer a charge of antimicrobial gel into the distal urethral cavity. The antimicrobial gel comprises an antimicrobial agent, which kills commensal bacteria within the distal urethral cavity, and acts as an antimicrobial barrier thereby helping to eradicate any bacteria that successfully enter the distal and proximal urethral cavity during sexual intercourse, thereby preventing transmission of bacteria to the proximal urethra and bladder. Once intercourse has concluded, the gel may be easily removed from the distal urethral cavity by urination.

The elongate member is the part of the device which may be inserted into the female distal urethral cavity. Optionally the elongate member is tapered to facilitate easy insertion.

The elongate member of the device may be formed from a soft and flexible material. For example, the elongate member may be formed from a silicone or silicone rubber material.

Optionally, the elongate member may be coated with an antimicrobial surface coating. Suitably, such a coating minimizes the likelihood of pathogens being transmitted into the urethra on the device.

The device may be formed from a silicone or silicone rubber material.

Alternatively, the device may be constructed of a flexible plastic or elastomer such as PVC, nitrile, polyisoprene, latex, rubber or any thermoplastic elastomer. The device may be integrally formed or formed from individual component parts which are subsequently assembled together. Preferably, the device is integrally formed.

Rigid polymers such as polypropylene can be used as long as the wall of the reservoir is thin enough to allow the reservoir to flex and deform in order to squeeze the composition (such as the antimicrobial gel) from the reservoir.

While the elongate member is dimensioned for insertion through an external urethral orifice, and is insertable into a distal urethral cavity, the deformable reservoir and collar remain outside of the body (i.e. outside of the urethra). The collar is designed to abut the urethral meatus, and prevents the elongate member from entering a proximal urethral cavity. For example, when the elongate member is inserted into the distal urethral cavity, the collar may abut the user's labia.

As outlined above, migration of bacteria from the distal urethral cavity to the proximal urethral cavity and up into the bladder can lead to infection. Thus it is essential, that when using the device bacteria are not inadvertently transferred into the proximal urethral cavity. Suitably, the elongate member may be from 15 mm to 40 mm in length. Advantageously, the collar ensures that any bacteria which may adhere to the device, cannot reach the proximal urethral cavity. Furthermore, the antimicrobial kills any such bacteria.

An antimicrobial may be stored in the deformable reservoir. The deformable reservoir may be integrally formed with the elongate member. The deformable reservoir may comprise a seal for retaining the antimicrobial in the reservoir (prior to use). This protects the antimicrobial from contamination. The seal may be broken for example by squeezing the deformable reservoir, thereby expelling the antimicrobial therefrom. By squeezing the deformable reservoir, the seal is broken, the antimicrobial flows into the elongate member and out of the pores of the elongate member. The reservoir may be bulbous or bulb shaped; the skilled person will appreciate that a range of shapes would be suitable. The reservoir may be easily squeezed/deformed using two fingers, such as a finger and a thumb. The external surface of the reservoir is preferably textured to provide the user with grip during use.

The antimicrobial is preferably an antimicrobial gel. The antimicrobial gel includes an antimicrobial agent for example an antiseptic, a metal ion solution or it may be an antibiotic.

In a preferred embodiment, the antimicrobial agent is an antiseptic such as chlorohexidine and is present in an antimicrobial gel composition at a concentration of 0.01 wt % or more and 1.0 wt % or less based on the total weight of the antimicrobial gel. Preferably, the chlorhexidine is present in the range of from 0.1 wt % to 0.3 wt % and most preferably in the range of from 0.2 wt % to 0.3 wt % based on the total weight of the antimicrobial gel.

Optionally, the antimicrobial gel may contain preservatives, viscosity modifiers and/or other modifiers such as stabilisers, perfumes and solvents. For example, the antimicrobial gel may contain preservatives such as methyl hydroxybenzoate and/or propyl hydroxybenzoate. Suitably, a preservative may be present at a concentration of less than 1.0 wt % based on the total weight of the antimicrobial gel. Advantageously, methyl hydroxybenzoate and propyl hydroxybenzoate also act as mild antimicrobials, which may assist with the bacteriostatic effects of the antimicrobial gel. The incorporation of antiseptics that irritate or sensitise mucosal tissues such as iodine or alcohol are to be avoided. Solid or semi-solid compositions are to be avoided as these will take time to dissolve and elute and may not be successfully deployed by the device during it's transient time within the urethra. Similarly, low viscosity fluid or liquid based mixtures may also not be efficacious as the fluid may flow out from the urethra over time and not provide the requisite protection thereafter. Preferably, the antimicrobial gel has a viscosity in the range of from 100 cP to 1000 cP when measured at 25° C., more preferably the viscosity is in the range of from 400 cP to 800 cP, even more preferably the viscosity is in the range of from 730 to 750 cP when measured at 25° C.

Suitably, the antimicrobial gel comprises a gel such as glycerol, hydroxyethyl cellulose, polyethylene glycol, propylene glycol, hyaluronic acid, chondroitin sulphate silicone, oils, petroleum jelly, water or combinations thereof. The gel may comprise a mixture of such materials which are mixed to produce the desired viscosity. The active antimicrobial agent, such as chlorohexidine, is preferably added at less than 1% based on the total weight of the antimicrobial gel, optionally additives and preservatives such as methyl hydroxybenzoate and/or propyl hydroxybenzoate may also be included.

When pressure is applied to the deformable reservoir, the antimicrobial is urged therefrom into the elongate member and out through the pores defined in the elongate member. The pores are apertures which extend through the walls of the elongate member.

Accordingly, in order for a female subject to topically apply the antimicrobial into their distal urethral cavity, the distal end of the elongate member is inserted through the external urethral orifice, into the distal urethral cavity. The collar prevents over insertion of the elongate member, as it abuts the urethral meatus (and depending on the size of the collar, the collar may also abut the *Labia minoris*). Once the elongate member is fully inserted in the distal urethral cavity, the subject may topically deliver the antimicrobial by squeezing the deformable reservoir which comprises the antimicrobial, urging the antimicrobial from the deformable reservoir, into the elongate member, and out through the pores defined in the elongate member into the distal urethral cavity. The pores defined along the length of the elongate member may be configured to facilitate circumferential application of the antimicrobial, coaxial with a longitudinal axis of the elongate member. Desirably, the elongate member may comprise a terminal orifice. When pressure is applied to the deformable reservoir, the antimicrobial will also be urged through the terminal orifice of the elongate member and be applied to the mid-urethral sphincter which partitions the distal urethral cavity from the proximal urethral cavity. Only a small portion of the gel is directed up into the upper, proximal urethra and the bulk of the gel is retained in the distal urethra. Once the antimicrobial has been delivered into the distal urethral cavity, the device may be removed and discarded. The viscosity of the gel is chosen such that the gel does not easily leak from the urethra, but may be readily flushed by urination.

The urethral antimicrobial delivery device is only in contact with the body for a short time, preferably less than 1 minute and is not therefore an implantable device. This short contact time eliminates any possible reactions from the local tissue to the device itself. The elongate member may be lubricated to facilitate insertion and removal from the urethral cavity. This may be achieved for example by expelling a small quantity of antimicrobial prior to insertion—the antimicrobial is urged through the pores and will function as a lubricant on the outer surface of the elongate member.

The topical application of an antimicrobial using the antimicrobial delivery device of the present invention has significant advantages in comparison to traditional insertion of medicaments into the urethra using syringes. For instance, the elongate member is dimensioned for insertion through an external urethral orifice, whereas a syringe will require additional attachments such as quills. Unlike the present device, the syringe having a tube attached thereto, to facilitate insertion through the urethral orifice is not configured to prevent over insertion of the tube. The presence of the collar in the present invention prevents over insertion of the elongate member, thereby ensuring the mid-urethral sphincter is not breached, and the antimicrobial is desirably, topically applied in the distal urethral cavity. Furthermore, a plastic tube attached to a syringe will deliver a medicament from the aperture at the terminus of the plastic tube, and topical application throughout the entire distal urethral cavity is not certain. A medicament being delivered by a syringe, will be expelled upwards, which may lead to the medicament being discharged into the proximal urethral cavity and bladder. In addition, the plastic tubes attached to a syringe may themselves act as a surface on which pathogens may be transmitted, if the plastic tube enters the proximal urethral cavity, such pathogens may be introduced into the proximal urethral cavity. Though it is intended that the device of the present invention be sterile, the elongate member and the collar are configured to ensure that the elongate member cannot enter the proximal urethral cavity, thereby precluding the possibility of the elongate member introducing pathogens into the proximal urethral cavity and cavity. Finally, it is difficult to physically manipulate a syringe for a female patient attempting to insert the gel into her own urethra as this would require her to push the syringe plunger with her fingers as opposed to her thumb. This is a complex and dexterous manoeuvre and would make it difficult for the patient to correctly maintain alignment of the syringe during deployment. With the antimicrobial delivery device of the present invention, the patient merely has to insert the elongate member into the distal urethral cavity, which operation is facile, owed to the customised dimensions of the device, and then the antimicrobial can be effectively delivered by gently squeezing the deformable reservoir to deploy the antimicrobial in the distal urethral cavity.

To aid with insertion of the barrier device, it is recommended that the external surfaces of the device be lubricated with a sterile lubricating gel. As outlined above, a preferred method is to lubricate the elongate member with the antimicrobial, such as an antimicrobial gel, by simply squeezing a small amount of the antimicrobial gel from the deformable reservoir. This also primes the system and ensures that no air resides in the line.

A preferred antimicrobial composition comprises:
chlorhexidine in an amount of from 0.1 wt % to 0.3 wt %;
hydroxyethyl cellulose in an amount of from 1 wt % to 3 wt %;
preservatives in an amount of from 0.01 wt % to 0.1 wt %;
propylene glycol in an amount of from 0.5 to 30 wt %; and
water in an amount of from 65 wt % to 96 wt %.

Suitably, said antimicrobial composition has a viscosity in the range of from 400 cP to 800 cP when measured at 25° C.

In an alternative embodiment, the device of the present invention may be employed to topically apply a composition comprising mannose in the distal urethral tract of a female subject.

The composition comprising mannose may be a gel.

Mannose may be present in the composition in concentrations of 0.01 wt % or more to 50 wt % or less, for example mannose may be added in a concentration of from 0.1 wt % or more, such as 0.5 wt % or more, or 1 wt % or more, for example 5 wt % or more based on the total weight of the composition. The mannose may be added in a concentration of 50 wt % or less such as 30 wt % or less, suitably 15 wt % or less, for example 10 wt % or less, or 8 wt % or less based on the total weight of the antimicrobial gel composition. For example, mannose may be present in a concentration of from 0.01 to 8 wt % based on the total weight of the antimicrobial gel composition. Without being bound by theory, it is thought that mannose may preferentially bind to virulent *E. coli* bacteria and thereby prevent them from migrating to the proximal urethra and into the bladder. The bacteria bound by the mannose in the gel may then be eliminated from the urethra by urination.

The gel may for example be a gel comprising glycerol, hydroxyethyl cellulose, polyethylene glycol, propylene glycol, hyaluronic acid, chondroitin sulphate silicone, oils, petroleum jelly, water or combinations thereof. The gel may comprise a mixture of such materials which are mixed to produce a gel of a preferred viscosity. The mannose may be added in concentrations as described above. Optionally additives and preservatives such as methyl hydroxybenzoate and/or propyl hydroxybenzoate may also be included.

Preferably, the gel comprising mannose has a viscosity in the range of from 100 cP to 1000 cP when measured at 25° C., more preferably the viscosity is in the range of from 400 cP to 800 cP, even more preferably the viscosity is in the range of from 730 to 750 cP when measured at 25° C.

Suitably, the device comprising a composition comprising mannose may be used to treat or prevent or reduce the likelihood of urinary tract infection in a female subject.

EXAMPLES

FIG. 1 is a perspective view of an antimicrobial delivery device of the present invention. The device 1 comprises a deformable reservoir (101) in fluid connection with an elongate member (102), the elongate member comprising a lumen (106), the elongate member having a proximal end (107) and a distal end (108), the elongate member having a plurality of pores (103) defined therein, said pores being distributed along a length of said elongate member, the elongate member being dimensioned for insertion through an external urethral orifice, whereby the elongate member is insertable into a distal urethral cavity for topical delivery of an antimicrobial in said distal urethral cavity, the device comprising a collar (105) to prevent said elongate member entering a proximal urethral cavity.

The embodiment depicted in FIG. 1 represents a device wherein the elongate member (102) is approximately 20 mm in length. The diameter of the elongate member (102) is approximately 3 mm. The pores (103) defined in the elongate member have a diameter of approximately 0.8 mm. The deformable reservoir (101) has an internal volume of approximately 2 mL.

Figure 2:
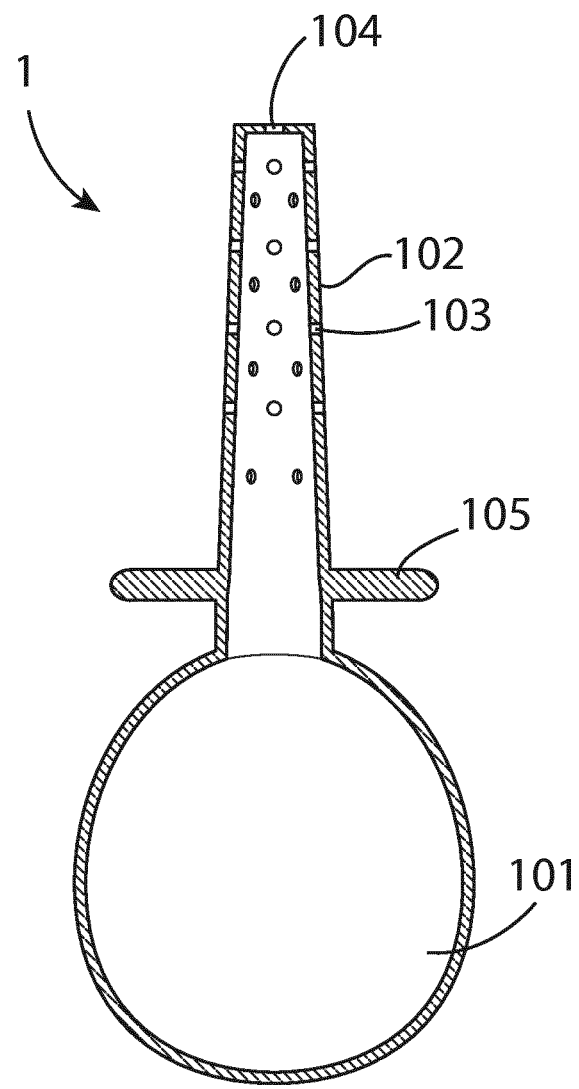
FIG. 2 is a cross-section view of the device of FIG. 1.
Figures 3A, 3B:
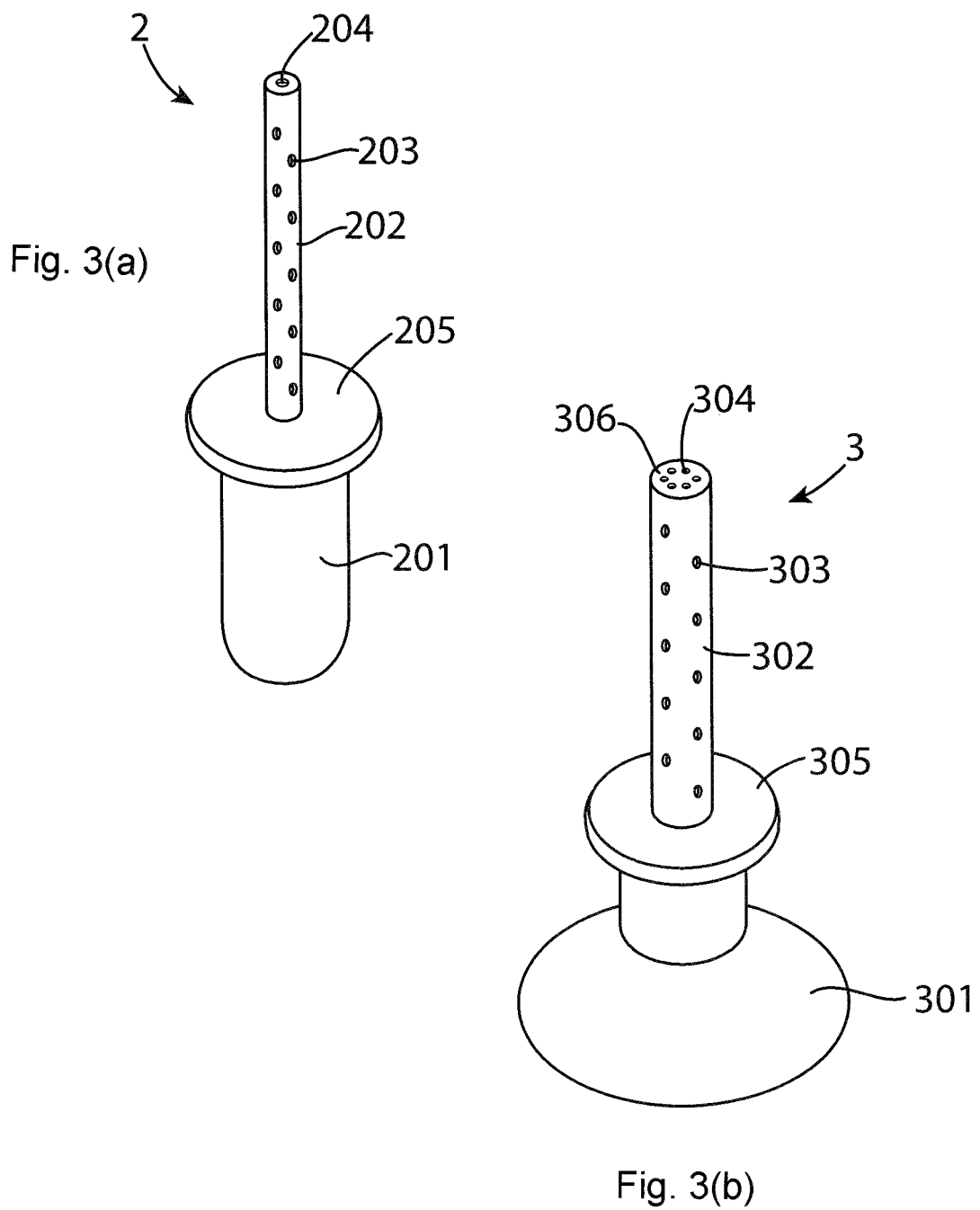
FIG. 3 is a perspective view of alternative embodiments of the antimicrobial delivery device.

FIG. 2 is a cross-section of the embodiment shown in FIG. 1. FIG. 3 illustrates two alternative embodiments of the present invention. The embodiment (2) of FIG. 3(*a*) comprises an elongate member 202 having pores (203) defined therein and comprising a terminal orifice (204) at a distal end of the elongate member. The collar (205) is circumferentially disposed about the proximal end of the elongate member. The collar is disposed approximately 15 mm from the terminus of the distal end of the elongate member.

The embodiment (2) shown in FIG. 3(*a*) comprises a deformable reservoir (201) having an internal volume of approximately 1.5 mL.

The embodiment (3) shown in FIG. 3(*b*) comprises a deformable reservoir (301) having an internal volume of approximately 3 mL. The embodiment of FIG. 3(*b*) comprises an elongate member (302) having a length of approximately 35 mm. The diameter of the elongate member is approximately 4 mm. The elongate member is capped by a terminal plate (306) having a plurality of terminal orifices (304) defined therein. The pores (303) have a diameter of approximately 1 mm. The terminal orifices have a diameter of approximately 0.1 mm. The collar (305) prevents the elongate member (302) entering the proximal urethral cavity of the female subject when the elongate member (302) is inserted into the distal urethral cavity.

Figure 4:
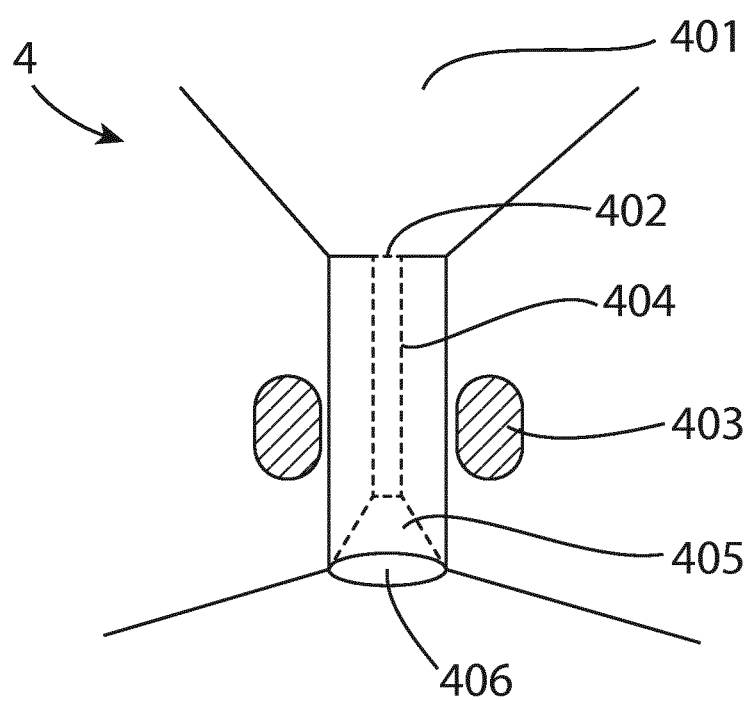
FIG. 4 is a schematic of the female urethra.

FIG. 4 is a schematic of the female urethra and bladder. The urethra transports urine from the bladder (401) to the outside of the body. The urethra comprises a lumen (402) and the urethra is partitioned into two regions, the distal urethra (405) and the proximal urethra (404). The mid-urethral sphincter (403) is positioned between the distal urethra and the proximal urethra. The opening to the urethra or urethral orifice (406) is the orifice through which the elongate member of the antimicrobial delivery device must enter.

The antimicrobial delivery device such as that shown in the embodiment of FIG. 1, comprises an elongate member in fluid connection with a deformable reservoir. The elongate member may be inserted through the urethral orifice (406) into the distal urethral cavity (405). The collar (105) abuts the urethral meatus and prevents over insertion of the elongate member (102) beyond the distal urethral cavity, into the proximal urethral cavity. The collar, may, for example, lie against the labia to prevent over-insertion of the elongate member. The deformable reservoir (101) may then be squeezed by the user to deploy the antimicrobial gel stored therein, from the deformable reservoir (101) via the elongate member (102), through the pores (103) and terminal orifice (104) into the distal urethral cavity (405). The antimicrobial is topically delivered in the distal urethral cavity. The elongate member may then be withdrawn from the distal urethral cavity by the user leaving the antimicrobial gel as a temporary physical barrier that minimises bacterial ascension by physically filling and blocking the distal urethral cavity, and further acts by directly eradicating bacteria that do enter the urethra through the antiseptic action of the antimicrobial gel.

The words "comprises/comprising" and the words "having/including" when used herein with reference to the present invention are used to specify the presence of stated features, integers, steps or components but do not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of treating, preventing or reducing the likelihood of urinary tract infection comprising employing a urethral delivery device to incorporate a temporary barrier within the distal urethral cavity of a female subject prior to engaging in sexual activity;
   wherein the urethral deliver device comprises:
   a deformable reservoir in fluid connection with an elongate member, the elongate member comprising a lumen, the elongate member having a proximal end and a distal end,
   the elongate member having a terminal orifice defined therein at the distal end of the elongate member, the elongate member being dimensioned for insertion through an external urethral orifice of a female subject, whereby the elongate member is insertable into a distal urethral cavity for delivery of an antimicrobial in said distal urethral cavity;
   wherein the temporary barrier is a gel which reduces the likelihood of bacterial migration into the proximal urethral cavity and into the bladder during intercourse.

2. The method of claim 1, wherein the elongate member comprises a plurality of pores defined therein, said pores being distributed along a length of said elongate member.

3. The method of claim 1, wherein the elongate member comprises a plurality of pores defined therein, said pores being distributed along a length of said elongate member and wherein the device comprises a collar to prevent said elongate member entering a proximal urethral cavity.

4. The method of claim 1, wherein the deformable reservoir comprises a seal for retaining an antimicrobial in the reservoir, and wherein said seal is breakable by a user squeezing the deformable reservoir.

5. The method of claim 1, wherein the elongate member comprises a plurality of pores defined therein, said pores being distributed along a length of said elongate member and wherein the device comprises a collar to prevent said elongate member entering a proximal urethral cavity; and
   wherein the deformable reservoir comprises a seal for retaining an antimicrobial in the reservoir, and wherein said seal is breakable by a user squeezing the deformable reservoir.

6. The method of claim 1, wherein the gel is water soluble, for example, a water soluble antimicrobial gel.

7. The method of claim 6, wherein the antimicrobial gel comprises at least one antimicrobial agent selected from the group consisting of antiseptics such as chlorhexidine, povidone-iodine, glutaraldehyde, chloroxylenol, silver ions benzalkonium chloride, cetylpyridinium chloride cetalkonium chloride, triclosan, lauric acid, benzethonium chloride, sodium hypochlorite and antibiotics such as neomycin, bacitracin, polymyxin, penicillin, mupirocin, fusidic acid and combinations thereof.

8. The method of claim 7, wherein the antimicrobial agent is present in the antimicrobial gel at a concentration in the range of from 0.01 wt % to 1.0 wt % based on the total weight of the antimicrobial gel, suitably the antimicrobial agent is present in the antimicrobial gel at a concentration in the range of from 0.01 wt % to 0.50 wt %, such as from 0.1 wt % to 0.3 wt % based on the total weight of the antimicrobial gel.

9. The method of claim 7, wherein the antimicrobial gel comprises:
   an antimicrobial agent in an amount of from 0.01 wt % to 1.0 wt % based on the total weight of the composition,
   a gelling agent in an amount of from 0.5 wt % to 30 wt % based on the total weight of the composition,
   and a pharmaceutically acceptable carrier.

10. The method of claim 6, wherein the antimicrobial gel comprises mannose.

11. The method of claim 10, wherein the mannose is present in a concentration of from 0.01 wt % to 8 wt % based on the total weight of the antimicrobial gel.

12. A method of treating, preventing or reducing the likelihood of urinary tract infection comprising employing an urethral antimicrobial delivery device, to apply an antimicrobial in a distal urethral cavity of a female subject;
   wherein the urethral deliver device comprises:
   a) a deformable reservoir in fluid connection with an elongate member, optionally wherein-said deformable reservoir and said elongate member being integrally formed,
   b) the elongate member comprising a single lumen, wherein the elongate member is of from 15 mm to 40 mm in length,
   c) the elongate member having a proximal end and a distal end, d) the elongate member having a plurality of pores defined therein, said pores being distributed along a length of said elongate member, e) the elongate member being dimensioned for insertion through an external urethral orifice of a female subject, f) whereby the elongate member is insertable into a distal urethral cavity for delivery of an antimicrobial in said distal urethral cavity, and g) wherein the device comprises a collar to prevent said elongate member entering a proximal urethral cavity; and wherein the antimicrobial is a water soluble antimicrobial gel which reduces the likelihood of bacterial migration into the proximal urethral cavity and into the bladder during intercourse.

13. The method of claim 12, wherein the antimicrobial delivery device comprises the antimicrobial gel.

14. The method of claim 12, comprising the steps of:
(i) inserting the distal end of the elongate member through the external urethral orifice of the female subject, into the distal urethral cavity; and
(ii) squeezing the deformable reservoir, which comprises an antimicrobial gel, to urge the antimicrobial gel from the deformable reservoir, into the elongate member and out through the pores into the distal urethral cavity of said subject, thereby topically applying said antimicrobial gel in said distal urethral cavity.

15. The method of claim 12, wherein the deformable reservoir comprises a seal for retaining an antimicrobial gel in the reservoir, and wherein said seal is breakable by a user squeezing the deformable reservoir.

16. The method of claim 12, wherein the deformable reservoir comprises a seal for retaining an antimicrobial gel in the reservoir, and wherein said seal is breakable by a user squeezing the deformable reservoir, and wherein squeezing the deformable reservoir breaks said seal, thereby allowing the antimicrobial to flow into the elongate member and out of the pores of the elongate member.

17. A method of treating, preventing or reducing the likelihood of urinary tract infection in a female subject comprising the following steps:
(i) providing an urethral antimicrobial delivery device, comprising:
a) a deformable reservoir in fluid connection with an elongate member, optionally, wherein said deformable reservoir and said elongate member being integrally formed,
b) the elongate member comprising a single lumen, wherein the elongate member is of from 15 mm to 40 mm in length,
c) the elongate member having a proximal end and a distal end,
d) the elongate member having a plurality of pores defined therein, said pores being distributed along a length of said elongate member,
e) the elongate member being dimensioned for insertion through an external urethral orifice of a female subject,
f) whereby the elongate member is insertable into a distal urethral cavity for delivery of an antimicrobial in said distal urethral cavity,
g) wherein the device comprises a collar to prevent said elongate member entering a proximal urethral cavity;
h) wherein the deformable reservoir comprises a seal for retaining an antimicrobial gel in the reservoir, and said seal being breakable by a user squeezing the deformable reservoir;
f) wherein the device comprises a water soluble antimicrobial gel comprising an antimicrobial agent selected from the group consisting of:
antiseptics such as chlorhexidine, povidone-iodine, glutaraldehyde, chloroxylenol, silver ions benzalkonium chloride, cetylpyridinium chloride cetalkonium chloride, triclosan, lauric acid, benzethonium chloride, sodium hypochlorite; and
antibiotics such as neomycin, bacitracin, polymyxin, penicillin, mupirocin, fusidic acid and combinations thereof;
wherein the antimicrobial agent is present in the antimicrobial gel at a concentration in the range of from 0.01 wt % to 1.0 wt % based on the total weight of the antimicrobial gel, suitably the antimicrobial agent is present in the antimicrobial gel at a concentration in the range of from 0.01 wt % to 0.50 wt %, such as from 0.1 wt % to 0.3 wt % based on the total weight of the antimicrobial gel;
(ii) inserting the distal end of the elongate member through the external urethral orifice of the female subject, into the distal urethral cavity;
(iii) squeezing the deformable reservoir, which comprises an antimicrobial gel, to urge the antimicrobial gel from the deformable reservoir, into the elongate member and out through the pores into the distal urethral cavity of said subject, thereby topically applying said antimicrobial gel in said distal urethral cavity and forming a temporary barrier within the distal urethral cavity of the subject which reduces the likelihood of bacterial migration into the proximal urethral cavity and into the bladder during intercourse; and
(iv) removing the antimicrobial delivery device.

18. The method of claim 17, wherein the wherein the antimicrobial gel comprises glycerol, hydroxyethyl cellulose, polyethylene glycol, propylene glycol, hyaluronic acid, chondroitin sulphate silicone, oils, petroleum jelly, water or combinations thereof.

19. The method of claim 17, wherein the antimicrobial gel comprises methyl hydroxybenzoate and/or propyl hydroxybenzoate.

* * * * *